(12) United States Patent
Chang et al.

(10) Patent No.: US 11,980,446 B2
(45) Date of Patent: May 14, 2024

(54) ORAL CAVITY SCANNING DEVICE AND METHOD

(71) Applicant: Quanta Computer Inc., Taoyuan (TW)

(72) Inventors: Jung-Wen Chang, Taoyuan (TW); Chin-Kang Chang, Taoyuan (TW); Chao-Ching Huang, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 438 days.

(21) Appl. No.: 17/504,808

(22) Filed: Oct. 19, 2021

(65) Prior Publication Data

US 2022/0369935 A1 Nov. 24, 2022

(30) Foreign Application Priority Data

May 24, 2021 (TW) .................................. 110118588

(51) Int. Cl.
*A61B 5/00* (2006.01)
*G06T 7/149* (2017.01)

(52) U.S. Cl.
CPC .......... *A61B 5/0088* (2013.01); *A61B 5/0079* (2013.01); *G06T 7/149* (2017.01); *A61B 2562/0219* (2013.01); *G06T 2207/30036* (2013.01)

(58) Field of Classification Search
None
See application file for complete search history.

(56) References Cited

U.S. PATENT DOCUMENTS

| 10,542,880 B2 * | 1/2020 | Wang | A61B 5/4547 |
| 2019/0011996 A1 * | 1/2019 | Sabina | G06F 3/017 |
| 2022/0343528 A1 * | 10/2022 | Lee | G06T 7/90 |

* cited by examiner

*Primary Examiner* — Dov Popovici
(74) *Attorney, Agent, or Firm* — McClure, Qualey & Rodack, LLP

(57) ABSTRACT

An oral cavity scanning device is provided in the invention. The oral cavity scanning device includes an image capturing unit, an IMU circuit and a processing unit. The image capturing unit obtains a first image and a second image. The IMU circuit obtains IMU information corresponding to the first image and the second image. The processing unit obtains a distance value between the first image and the second image. The processing unit uses a contour algorithm to obtain a first contour and a second contour. The processing unit obtains first sampling points according to the first contour and second sampling points according to the second contour. The processing unit uses a feature algorithm to find relative feature points between the first sampling points and the second sampling points. The processing unit uses a depth information algorithm to obtain the depth information of each feature point.

10 Claims, 4 Drawing Sheets

ORAL CAVITY SCANNING DEVICE AND METHOD

CROSS REFERENCE TO RELATED APPLICATIONS

This Application claims priority of TW Patent Application No. 110118588 filed on May 24, 2021, the entirety of which is incorporated by reference herein.

BACKGROUND OF THE INVENTION

Field of the Invention

The invention generally relates to oral cavity scanning technology, and more particularly, to oral cavity scanning technology in which a depth algorithm is used to establish a 3-dimensional (3D) image of the oral cavity according to the information obtained by an oral cavity scanning device.

Description of the Related Art

As technology has progressed, oral cavity scanning applications are being applied more widely. The oral cavity scanning results can be used to establish an image for the patient's whole oral cavity. The doctor can let the patient know the state of his teeth according to the established image. Therefore, how to generate an oral cavity scanning result more accurately is a subject that is worthy of discussion.

BRIEF SUMMARY OF THE INVENTION

An oral cavity scanning device and method are provided to overcome the problems mentioned above.

An embodiment of the invention provides an oral cavity scanning device. The oral cavity scanning device comprises an image capturing unit, an inertial measurement unit (IMU) circuit, and a processing unit. The image capturing unit obtains a first image and a second image. The IMU circuit obtains IMU information corresponding to the first image and the second image. The processing unit obtains the first image and the second image from the image capturing unit and it obtains the IMU information from the IMU circuit. The processing unit obtains a distance value between the first image and the second image according to the IMU information. The processing unit uses a contour algorithm to obtain a first contour corresponding to a first target object in the first image and a second contour corresponding to a second target object in the second image. The processing unit obtains a plurality of first sampling points according to the first contour and a plurality of second sampling points according to the second contour. The processing unit uses a feature algorithm to find relative feature points between the first sampling points and the second sampling points. The processing unit uses a depth information algorithm to obtain depth information from each feature point according to the distance value and position information of the feature points.

In some embodiments of the invention, the oral cavity scanning device further comprises a light source unit. The light source unit provides a light source to the image capturing unit.

In some embodiments of the invention, the processing unit obtains a plurality of first sub-contours corresponding to the first target object by scaling down the first contour proportionally and obtains the first sampling points from the first contour and the first sub-contours; and the processing unit obtains a plurality of second sub-contours corresponding to the second target object by scaling down the second contour proportionally, and it obtains the second sampling points from the second contour and the second sub-contours. Then, the processing unit uses the feature algorithm to find the relative feature points from the first sampling points and the second sampling points.

In some embodiments of the invention, the processing unit obtains a 3D image according to the IMU information and the position information and depth information of the feature points.

An embodiment of the invention provides an image positioning method. The oral cavity scanning method is applied to an oral cavity scanning device. The oral cavity scanning method comprises the following steps. A first image and a second image are obtained by an image capturing unit of the oral cavity scanning device. IMU information corresponding to the first image and the second image are obtained by an IMU circuit of the oral cavity scanning device. The distance value between the first image and the second image are obtained according to the IMU information by a processing unit of the oral cavity scanning device. The processing unit uses a contour algorithm to obtain a first contour corresponding to a first target object in the first image and a second contour corresponding to a second target object in the second image. The processing unit obtains a plurality of first sampling points according to the first contour and a plurality of second sampling points according to the second contour. The processing unit uses a feature algorithm to find relative feature points between the first sampling points and the second sampling points. The processing unit uses a depth information algorithm to obtain the depth information of each feature point according to the distance value and the position information of the feature points.

Other aspects and features of the invention will become apparent to those with ordinary skill in the art upon review of the following descriptions of specific embodiments of an oral cavity scanning device and method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
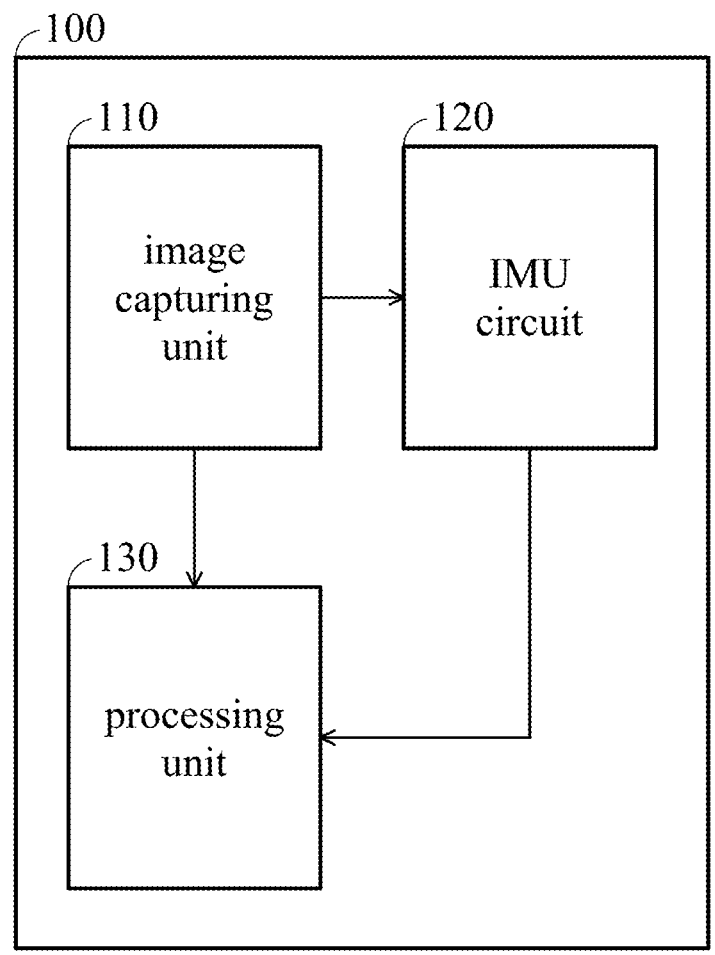
FIG. 1 is a block diagram of an oral cavity scanning device 100 according to an embodiment of the invention.

FIG. 1 is a block diagram of an oral cavity scanning device 100 according to an embodiment of the invention. As shown in FIG. 1, the oral cavity scanning device 100 may comprise an image capturing unit 110, an inertial measurement unit (IMU) circuit 120 and a processing unit 130. It should be noted that FIG. 1 presents a simplified block diagram in which only the elements relevant to the invention are shown. However, the invention should not be limited to what is shown in FIG. 1. The oral cavity scanning device 100 may also comprise other elements and the connections between the elements may be different from the oral cavity scanning device 100. According to an embodiment of the invention, the oral cavity scanning device 100 may be a dental mirror, but the invention should not be limited thereto.

According to an embodiment of the invention, the processing unit 130 may be also equipped in another electronic device (e.g. notebook, camera, but the invention should not be limited thereto), and the processing unit 130 may obtain the related information of the oral cavity scanning from the oral cavity scanning device 100 for the following operations of establishing the 3D image. In the embodiment, the oral cavity scanning device 100 may transmit the related information of the oral cavity scanning to the electronic device through a wireless communication method, e.g. Bluetooth, Wi-Fi or mobile communication (cellular network), but the invention should not be limited thereto.

According to an embodiment of the invention, the oral cavity scanning device 100 may also comprise a storage device (not shown in figures). The storage device may be a volatile memory (e.g. Random Access Memory (RAM)), or a non-volatile memory (e.g. flash memory, Read Only Memory (ROM)), a hard disk, or a combination of the above memory devices. The storage device 110 may store the data and files for scanning the oral cavity.

According to the embodiments of the invention, the image capturing unit 110 may be a built-in camera of the oral cavity scanning device 100. The image capturing unit 110 may be configured to capture the image data and provide the captured image data to the processing unit 130 or store the captured image data in a storage device (not shown in figures). According to an embodiment of the invention, the oral cavity scanning device 100 may comprise a light source unit (not shown in figures). The light source unit may be configured to provide light source to illuminate when the image capturing unit 110 is capturing the image data. The image capturing unit 110 may capture image data regarding to the oral cavity under the light source to scan the oral cavity.

According to an embodiment of the invention, the IMU circuit 120 may be an IMU chip. The IMU circuit 120 may comprise a gyroscope and an accelerator used to obtain the position, angle and moving information of the lens of the image capturing unit 110 when the image capturing unit 110 is capturing different image data.

Figure 2:
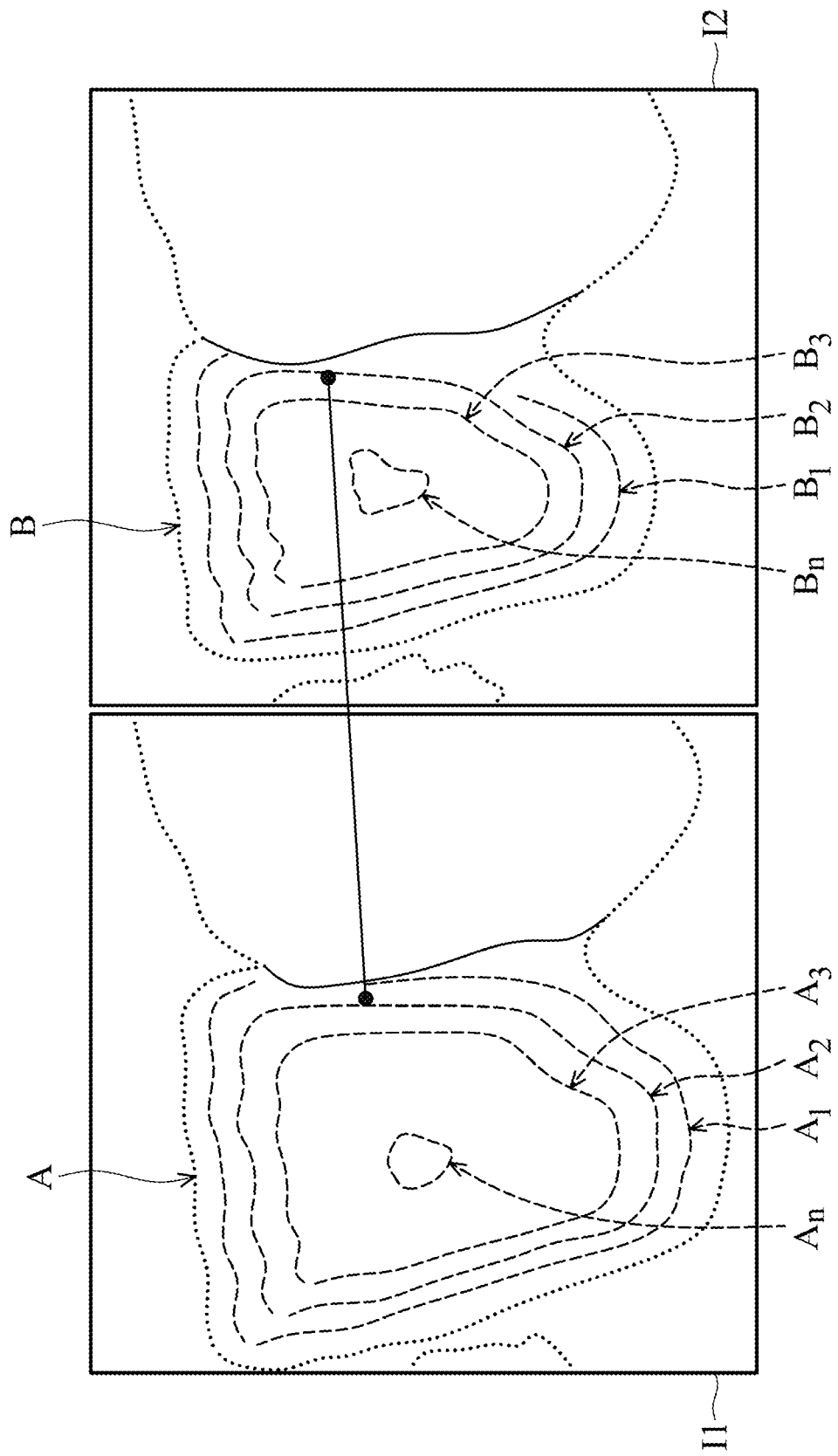
FIG. 2 is a schematic diagram illustrating a contour of a target object in the first image and the second image according to an embodiment of the invention.

According to an embodiment of the invention, when an oral cavity needs to be scanned to establish the 3D image of the oral cavity, the user may use the oral cavity scanning device 100 to scan the oral cavity in sequence (e.g. scan the upper jaw and the lower jaw of the oral cavity from left to right) to generate a plurality of oral cavity images (e.g. the first image I1 and the second image I2 shown in FIG. 2, but the invention should not be limited thereto). Specifically, when the user uses the oral cavity scanning device 100 to scan the oral cavity, the image capturing unit 110 may capture a plurality of the oral cavity images at different time points. At different time points, the image capturing unit 110 may be moved to different positions of the oral cavity to capture the oral cavity images corresponding to different oral cavity areas. When the image capturing unit 110 captures the images, the IMU circuit 120 may obtain the IMU information of each image. The IMU information may comprise the position, angle and moving information of the lens of the image capturing unit 110.

According to the embodiments of the invention, after the image capturing unit 110 captures the images, the processing unit 130 may obtain each image from the image capturing unit 110 (or a storage unit) and obtain the IMU information corresponding to each image (i.e. the position, angle and moving information of the lens of the image capturing unit 110) from the IMU circuit 120 (or a storage unit).

According to the embodiments of the invention, the processing unit 130 may obtain a distance value corresponding to each image and the one that comes next according to the IMU information corresponding to the lens of the image capturing unit 110 (i.e. the position, angle and moving information of the lens of the image capturing unit 110). Specifically, the processing unit 130 may obtain a position variation between a first image and a second image (i.e. the distance value corresponding to the first image and a second image) according to the IMU information of the first image and the IMU information of the second image, wherein the first image is generated by the image capturing unit 110 at a time point and the second image generated by the image capturing unit 110 at the next time point.

In addition, according to the embodiments of the invention, the processing unit 130 may use a contour algorithm (e.g. OpenCV-python edge detection, but the invention should not be limited thereto) to obtain a contour and a plurality of sub-contours corresponding to a target object (e.g. tooth) in each image. Taking FIG. 2 as an example, FIG. 2 is a schematic diagram illustrating a contour of a target object in the first image and the second image according to an embodiment of the invention. As shown in FIG. 2, the processing unit 130 may use the contour algorithm to obtain the contour A (shown by dashed lines) of the teeth in the first image I1 and the contour B (shown by dashed lines) of the teeth in the second image I2. Then, as shown in FIG. 2, after the processing unit 130 obtains the contour A of the teeth in the first image I1 and the contour B of the teeth in the second image I2, the processing unit 130 may obtain the sub-contours (i.e. sub-contours $A_1 \sim A_n$ and sub-contours $B_1 \sim B_n$) corresponding the teeth in the first image I1 and the second image I2 by scaling down the contour A of the teeth in the first image I1 and the contour B of the teeth in the second image I2 proportionally. In the embodiment, scaling down the contour A and the contour B proportionally means that the processing unit 130 may divide the teeth into a plurality of circles from the center of the teeth to the outermost circle of the teeth according to a shift parameter (e.g. 10%, but the invention should not be limited thereto) and obtain the sub-contour of each circle. For example, if the shift parameter is 10%, the processing unit 130 may scale down the contour A by 10% to obtain the sub-contour $A_1$, but the invention should not be limited thereto.

Figure 3:
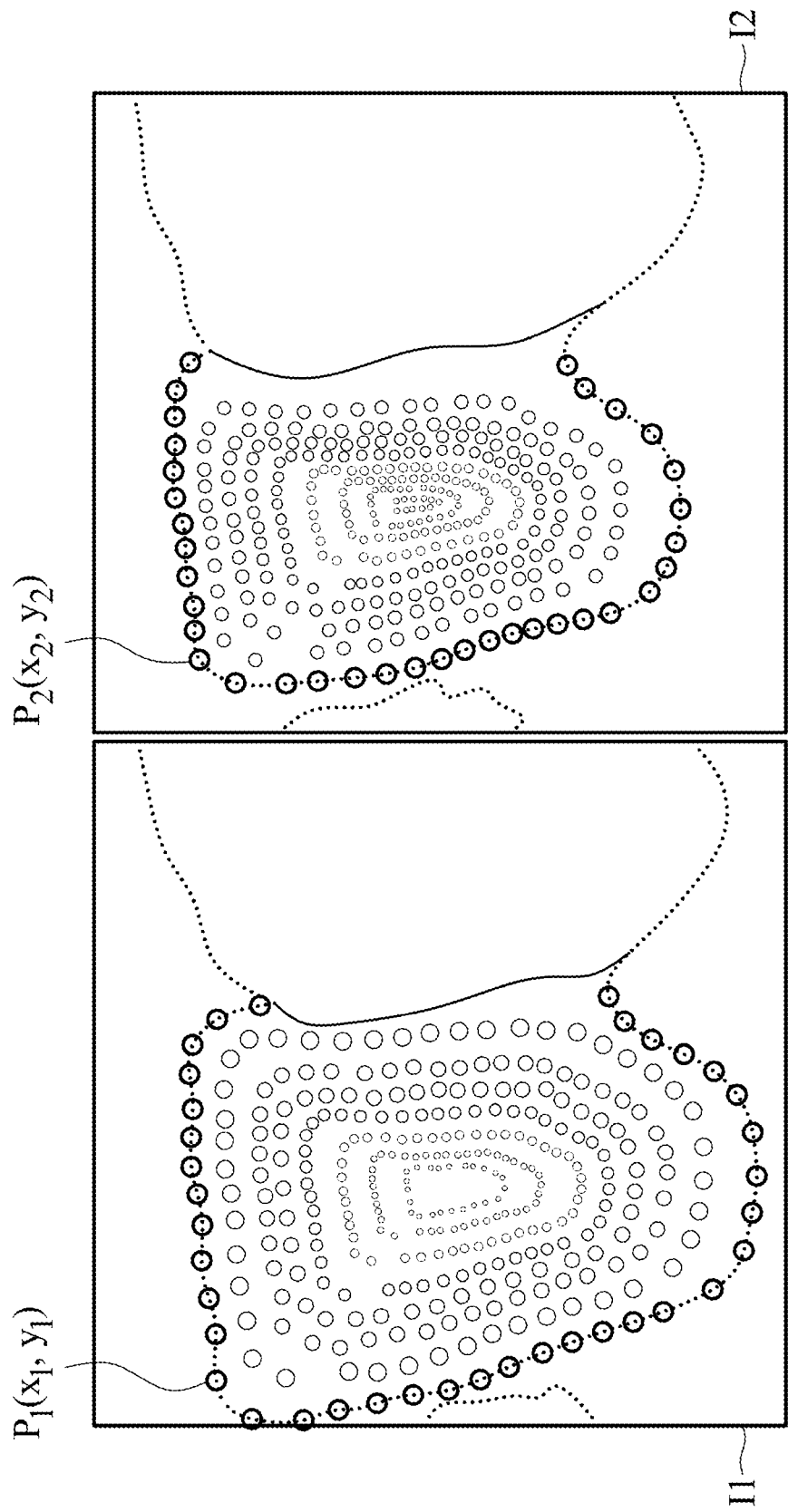
FIG. 3 is a schematic diagram illustrating a plurality of sampling points of a target object in the first image and the second image according to an embodiment of the invention.

According to the embodiments of the invention, after the processing unit 130 obtains the contour and sub-contours corresponding to the target object of each image, the processing unit 130 may obtain a plurality of sampling points in each contour and each sub-contour. Taking FIG. 3 as an example, FIG. 3 is a schematic diagram illustrating a plurality of sampling points of a target object in the first image and the second image according to an embodiment of the invention. As shown in FIG. 3, the processing unit 130 may obtain 40 sampling points in each contour and each sub-contour of the teeth in the first image I1 and the second image I2, but the invention should not be limited thereto.

According to the embodiments of the invention, after the processing unit 130 obtains the sampling points in each contour and each sub-contour in each image, the processing unit may use a feature algorithm (e.g. OpenCV Feature2D algorithm, but the invention should not be limited thereto) to find the relative feature points from the sampling points in an image and the sampling points in next image of the image. If the target object is tooth, the processing unit 130 may use the feature algorithm to find the relative feature points from the sampling points in an image and the sampling points in next image of the image according to the curvature, tartar shape, tooth decay, chipped tooth of the teeth. That is to say, the processing unit 130 may use the feature algorithm to determine whether the teeth in an image are the same as the teeth in the next image. Taking FIG. 3 as an example, the processing unit 130 may use the feature algorithm to determine that the sampling point $P_1$ in the first image I1 and the second sampling point $P_2$ in the second image I2 are relative feature points.

According to the embodiments of the invention, after the processing unit 130 obtains the relative feature points of an image and the following image, the processing unit 130 may use a depth information algorithm (e.g. binocular depth information algorithm) to obtain the depth information of each feature point according to the distance value corresponding to each image and the one that comes next (i.e. the position variation between each image and the one that comes next) and the position information of the feature points (e.g. the coordinates of the feature points). The depth information algorithm may be presented by the following equation:

$$Z = f - \frac{fD_x}{x_2 - x_1} = f - \frac{fD_y}{y_2 - y_1},$$

wherein Z means a depth of a feature point, f means the focal length of the image capturing unit 110, $D_x$ means the x-direction distance value between one image and the next, $x_1$ means a x-coordinate of a feature point in an image, $x_2$ means the x-coordinate of the feature point in next image, $D_y$ means the y-direction distance value between one image and the next, $y_1$ means a y-coordinate of a feature point in an image, and $y_2$ means the y-coordinate of the feature point in next image. Taking FIG. 3 as an example, when the sampling point $P_1$ in the first image I1 and the second sampling point $P_2$ in the second image I2 are relative feature points, the coordinate of the sampling point $P_1$ is $(x_1, y_1)$ and the coordinate of the sampling point $P_2$ is $(x_2, y_2)$, the processing unit 130 may substitute the coordinate of the sampling point $P_1$ and the sampling point $P_2$ into the equation to obtain the depth (i.e. Z) corresponding to the sampling point $P_1$.

It should be noted that the images of FIG. 2 and FIG. 3 merely show one plane of the teeth, but the invention should not be limited thereto. The oral cavity scanning device 100 may also obtain the images of other planes of the teeth and obtain the depth information of the feature points in these images.

After the processing unit 130 obtains the depth information of the feature points, the processing unit 130 may obtain a 3D image corresponding to each image according to the IMU information of each image and the position information and depth information of the feature points of each image. Then, the processing unit 130 may combine or assemble all 3D images to generate a 3D image corresponding to the oral cavity.

Figure 4:
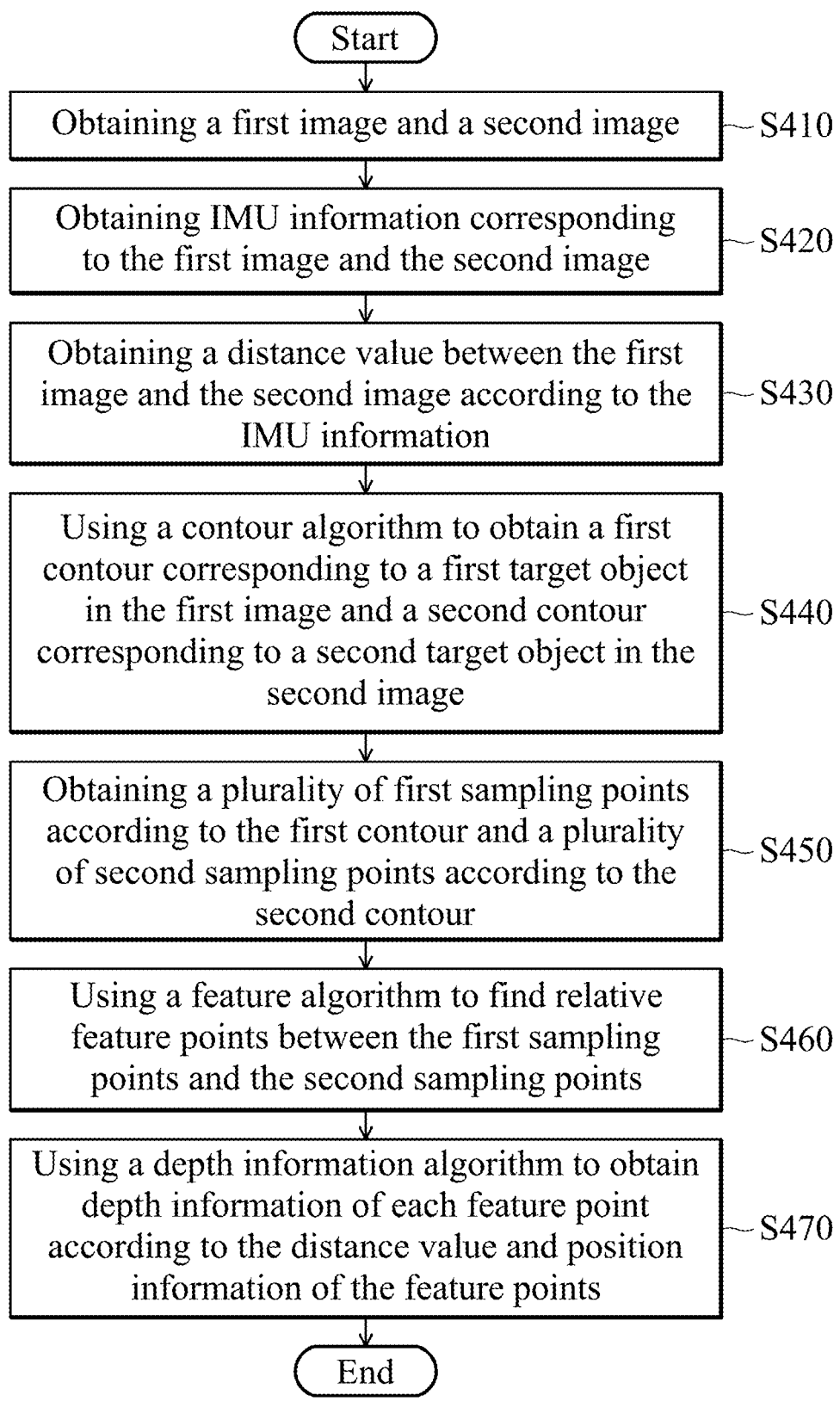
FIG. 4 is a flow chart illustrating an oral cavity scanning method according to an embodiment of the invention.

FIG. 4 is a flow chart illustrating an oral cavity scanning method according to an embodiment of the invention. The oral cavity scanning method can be applied to the oral cavity scanning device 100. As shown in FIG. 4, in step S410, an image capturing unit of the oral cavity scanning device 100 obtains a first image and a second image.

In step S420, an IMU circuit of the oral cavity scanning device 100 generates the IMU information corresponding to the first image and the second image.

In step S430, a processing unit of the oral cavity scanning device 100 obtains a distance value corresponding to the first image and the second image according to the IMU information.

In step S440, the processing unit of the oral cavity scanning device 100 uses a contour algorithm to obtain a first contour corresponding to a first target object in the first image and a second contour corresponding to a second target object in the second image.

In step S450, the processing unit of the oral cavity scanning device 100 obtains a plurality of first sampling points according to the first contour and a plurality of second sampling points according to the second contour.

In step S460, the processing unit of the oral cavity scanning device 100 uses a feature algorithm to find the relative feature points between the first sampling points and the second sampling points.

In step S470, the processing unit of the oral cavity scanning device 100 uses a depth information algorithm to obtain the depth information of each feature point according to the distance value and the position information of the feature points.

According to an embodiment of the invention, in the oral cavity scanning method, a light source device of the oral cavity scanning device 100 may provide a light source to the image capturing unit.

According to an embodiment of the invention, in the oral cavity scanning method, in steps S450~S460, the processing unit of the oral cavity scanning device 100 may further obtain a plurality of first sub-contours corresponding to the first target object by scaling down the first contour proportionally and obtain the first sampling points from the first contour and the first sub-contours. In addition, the processing unit of the oral cavity scanning device 100 may further obtain a plurality of second sub-contours corresponding to the second target object by scaling down the second contour proportionally and obtain the second sampling points from the second contour and the second sub-contours. Then, the processing unit of the oral cavity scanning device 100 may use the feature algorithm to find the relative feature points between the first sampling points and the second sampling points.

According to an embodiment of the invention, the step of the oral cavity scanning method may further comprises that the processing unit of the oral cavity scanning device 100 may obtain a 3D image according to the IMU information and the position information and depth information of the feature points.

According to the oral cavity scanning method provided in the invention, a 3D image of the oral cavity can be established according to the information obtained by the image capturing unit and the IMU circuit of the oral cavity scanning device.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects. Obviously, the teaching of the invention can be accomplished by many methods, and any specific configurations or functions in the disclosed embodiments only present a representative condition. Those who are skilled in this technology will understand that all of the disclosed aspects in the invention can be applied independently or be incorporated.

While the invention has been described by way of example and in terms of preferred embodiment, it should be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. An oral cavity scanning device, comprising:
   an image capturing unit, obtaining a first image and a second image; and
   an inertial measurement unit (IMU) circuit, obtaining IMU information corresponding to the first image and the second image; and
   a processing unit, obtaining the first image and the second image from the image capturing unit and obtaining the IMU information from the IMU circuit,
   wherein the processing unit obtains a distance value between the first image and the second image according to the IMU information,
   wherein the processing unit uses a contour algorithm to obtain a first contour corresponding to a first target object in the first image and a second contour corresponding to a second target object in the second image,
   wherein the processing unit obtains a plurality of first sampling points according to the first contour and a plurality of second sampling points according to the second contour,
   wherein the processing unit uses a feature algorithm to find relative feature points between the first sampling points and the second sampling points, and
   wherein the processing unit uses a depth information algorithm to obtain depth information from each feature point according to the distance value and position information of the feature points.

2. The oral cavity scanning device of claim 1, further comprising:
   a light source unit, provide a light source to the image capturing unit.

3. The oral cavity scanning device of claim 1, wherein the processing unit obtains a plurality of first sub-contours corresponding to the first target object by scaling down the first contour proportionally and obtains the first sampling points from the first contour and the first sub-contours; and the processing unit obtains a plurality of second sub-contours corresponding to the second target object by scaling down the second contour proportionally and obtains the second sampling points from the second contour and the second sub-contours.

4. The oral cavity scanning device of claim 3, wherein the processing unit uses the feature algorithm to find the relative feature points from the first sampling points and the second sampling points.

5. The oral cavity scanning device of claim 1, wherein the processing unit obtains a 3D image according to the IMU information and the position information and the depth information of the feature points.

6. An oral cavity scanning method, applied to an oral cavity scanning device, comprising:
   obtaining, by an image capturing unit of the oral cavity scanning device, a first image and a second image;
   obtaining, by an Inertial measurement unit (IMU) circuit of the oral cavity scanning device, IMU information corresponding to the first image and the second image;
   obtaining, by a processing unit of the oral cavity scanning device, a distance value between the first image and the second image according to the IMU information;
   using, by the processing unit, a contour algorithm to obtain a first contour corresponding to a first target object in the first image and a second contour corresponding to a second target object in the second image;
   obtaining, by the processing unit, a plurality of first sampling points according to the first contour and a plurality of second sampling points according to the second contour;
   using, by the processing unit, a feature algorithm to find relative feature points between the first sampling points and the second sampling points; and
   using, by the processing unit, a depth information algorithm to obtain depth information of each feature point according to the distance value and position information of the feature points.

7. The oral cavity scanning method of claim 6, further comprising:
   providing, by a light source unit of the oral cavity scanning device, a light source to the image capturing unit.

8. The oral cavity scanning method of claim 6, further comprising:
   obtaining, by the processing unit, a plurality of first sub-contours corresponding to the first target object by scaling down the first contour proportionally;
   obtaining, by the processing unit, the first sampling points from the first contour and the first sub-contours;
   obtaining, by the processing unit, a plurality of second sub-contours corresponding to the second target object by scaling down the second contour proportionally; and obtaining, by the processing unit, the second sampling points from the second contour and the second sub-contours.

9. The oral cavity scanning method of claim 8, further comprising:
using, by the processing unit, the feature algorithm to find the relative feature points from the first sampling points and the second sampling points.

10. The oral cavity scanning method of claim 6, further comprising:
obtaining, by the processing unit, a 3D image according to the IMU information and the position information and the depth information of the feature points.

* * * * *